United States Patent [19]

Sanderson et al.

[11] 4,436,932

[45] Mar. 13, 1984

[54] ALKANE ACETATES PRODUCED BY OXIDATIVE ESTERIFICATION OF OLEFINS OVER AMMONIUM BORATE IN THE PRESENCE OF A CARBOXYLATE ION SOURCE

[75] Inventors: John R. Sanderson, Austin; Steven H. Vanderpool, New Braunfels; Lewis W. Watts, Jr., Austin, all of Tex.

[73] Assignee: Texaco Inc., White Plains, N.Y.

[21] Appl. No.: 402,686

[22] Filed: Jul. 28, 1982

[51] Int. Cl.$^3$ ............................................. C07C 67/05
[52] U.S. Cl. .................................................. 560/246
[58] Field of Search ............... 560/241, 243, 244, 245, 560/246, 247

[56] References Cited

U.S. PATENT DOCUMENTS 4,220,800  9/1980  Stapp ................................... 560/246

*Primary Examiner*—Michael L. Shippen
*Attorney, Agent, or Firm*—Robert A. Kulason; Jack H. Park; David L. Mossman

[57] ABSTRACT

A process for the production of alkane acetates from olefins in the presence of an ammonium borate catalyst, oxygen and a carboxylate ion source via oxidative esterification is described. The reaction is conducted at a temperature in the range of 80° to 280° C. and a pressure of 1 atmosphere or greater. Alkane diacetates and hydroxy acetates are produced which may be used as precursors to alkylene oxides, alkylene glycols and other useful compounds.

10 Claims, No Drawings

BACKGROUND OF THE INVENTION

1. Field of the Invention

The invention is related to a process for the production of alkane acetates by the oxidative esterification of olefins, and is particularly related to such a process conducted in the presence of a carboxylate ion source temperature of between 425° to 575° C., an oxygen volume percent of between 4 and 14, a contact time with the oxygen of between 0.07-1.5 seconds, a pressure of between 20 to 150 psig and constant concentrations of reactants. Epoxides may also be produced from olefins and oxygen which are in an inert reaction medium when they are brought in contact with a rhenium catamade by passing olefins in oxygen in an alkanoic acid medium over cerium salts. A method for making glycol esters from olefins and oxygen in a carboxylic acid medium over tellurium and an appropriate form of bromine is revealed in U.S. Pat. No. 3,668,239. British Pat. No. 1,278,353 teaches that non-vicinal glycols may be reacted with carbon monoxide over a rhodium or iridium catalyst together with a halogen promoter to produce dicarboxylic acids which are precursors to diesters which are intermediates to the epoxides. Further, British Pat. No. 1,326,219 discloses that glycol esters may be produced from olefins and oxygen in the presence of at least one carboxylic acid when a halogen is employed as an anion and a metal cation is present which is selected from the group of tellurium, cerium, antimony, manganese, arsenic or cobalt. Other examples which reveal how esters may be made from olefins include U.S. Pat. No. 3,770,813 where an olefin with a chloro, hydroxy or lower alkanoyloxy substituent together where the cation is zirconium, niobium, molybdenum, hafnium, tantalum, tungsten or rhenium where the anion is a halide in the presence of lithium, sodium, potassium, titanium, vanadium, chromium, manganese, iron, cobalt, nickel, copper, zinc, aluminum or silver.

Some of the more recent patents in this field include the following. Esters may be produced from olefins in an acid plus oxygen over a tin or cerium catalyst in the presence of iodide as revealed by U.S. Pat. No. 4,154,957. Saturated vicinal esters may be produced from olefins, carboxylic acids and oxygen in the presence of a boron-containing catalyst according to the invention of U.S. Pat. No. 4,220,800. U.S. Pat. No. 4,221,916 teaches that olefins, carboxylic acids and oxygen when reacted together over a vanadium or ruthenium-containing catalyst can also produce saturated vicinal esters. U.S. Pat. No. 4,238,624 discloses a procedure by which ethylene, oxygen and a lower alkanoic acid are reacted together over an iodine source in a bismuth No. 3,789,065. The residue is then contacted with a carboxylic acid to yield additional vicinal glycol esters. British Pat. No. 1,353,814 describes the reaction of olefins and oxygen in a carboxylic acid in the liquid phase that contains at least 0.5 percent water over a catalyst system identical to that of the patent previously described to also yield vicinal glycol esters. Ethylene or propylene may be reacted with oxygen in a carboxylic acid over a catalyst system comprising a tellurium cation and a bromide anion or a selenium cation plus a chloride or bromide anion to produce vicinal glycol esters as revealed in U.S. Pat. No. 3,907,874.

Aliphatic hydrocarbon carboxylic acid esters of vicinal glycols which contain organic halogen impurities may be purified by passing them over aquobasic alkali metal compounds, aquobasic earth metal compounds or compounds (other than halides) of zinc, lead, cadmium, tin, mercury, silver, manganese, copper, nickel, cobalt, iron or chromium in accordance with the invention in British Pat. No. 1,410,834. German Auslegeschrift No. 2,430,022 describes a multi-step procedure for producing butane diols, which are precursors to butane oxide, from propylene, oxygen and acetic acid.

A system which has obtained a fair amount of commercial importance is described in U.S. Pat. No. 4,045,477 by which vicinal hydroxy esters and diesters are produced from olefins and oxygen over tellurium and an iodide source. Organic monoesters of vicinal glycols may also be produced from olefins, oxygen, water and a carboxylic acid over a system comprising an iodine compound (such as copper iodide, manganese iodide or cerium iodide), a copper compound, and an activated ion taken from the group of manganese, cerium, alkali metals, alkali earth metals, nitric compounds or mixtures thereof, according to the invention in U.S. Pat. No. 4,061,868. U.S. Pat. No. 4,069,381 reveals how glycol monoesters may be made from olefins, oxygen and carboxylic acids over a catalyst system 4,012,423 describes how vicinal hydroxy esters may be reacted over group I, II and IIIA basic metal carboxylates, being the preferred catalyst (sodium, potassium, lithium, calcium or barium, etc.), or group I, II and IIIA basic metal simple oxides and complex oxides and organic bases (such as borates, phosphates, oxides and carboxylates, particularly sodium borate, nickel oxide, etc.) to give epoxides. Another method is described in U.S. Pat. No. 4,158,008 whereby propylene glycol monoesters in the presence of a high boiling solvent is reacted over a base to produce propylene oxide. Propylene oxide may also be produced from propylene glycol with the removal of a water molecule over a weakly acidic carrier comprising a basic alkali metal salt of a low molecular weight carboxylic acid as taught by U.S. Pat. No. 4,226,780.

Of the numerous patents discussed so far, the ones considered to be most relevant to the invention at issue are U.S. Pat. Nos. 4,012,423; 4,069,381 and 4,220,800, all of which have been discussed.

Despite all of the investigative routes described so far and the ones that have been devised which have not been described, there is still a need for an efficient method for making propylene oxide from propylene, in addition to making the alkylene oxides from other olefins, which does not involve a highly corrosive or highly expensive catalyst system.

SUMMARY OF THE INVENTION

The invention concerns a process for the production of alkane acetates comprising reacting an olefin or a mixture of olefins with oxygen and a carboxylate ion source in the presence of ammonium borate.

DETAILED DESCRIPTION OF THE PREFERRED EMBODIMENTS

Alkane hydroxy acetates and diacetates, also called glycol monoesters or diesters or vicinal diesters, may be prepared by the oxygen or air oxidation of olefins in a solvent capable of generating a carboxylate ion in the presence of ammonium borate. The diacetates may be converted to epoxides or glycols using methods known in the art, some of which have been outlined previously. Both the epoxides and the glycols are of interest in the manufacture of important high volume products, including urethane polyols, gasoline additives, and heat transfer fluids.

According to the method of this invention, the olefin feedstocks may consist of any mono olefin having the double bond located anywhere within the molecule and mixtures of such olefins. The olefin may be an alpha or an internal olefin. Specific examples of suitable feedstocks include, but are not limited by, the following list: propylene, 1-butene, 2-butene, 1-pentene, 2-pentene, 1-hexene, 2-hexene, 3-hexene, heptenes, octenes, nonenes, decenes, undecenes, dodecenes, tridecenes such as 6-tridecene, tetradecenes such as 7-tetradecene, pentadecenes, hexadecenes, etc., and mixtures thereof. Preferably, the olefin has 3 to 16 carbon atoms. Propylene is especially preferred.

Of course, molecular oxygen in a pure form or air is an essential co-reactant for the method of this invention.

The co-reactant and solvent must be a compound capable of generating a carboxylate ion when it serves as a solvent. These compounds may be generally described as carboxylic acids or anhydrides. They may include materials such as acetic acid, acetic anhydride, carboxylic acids, although acetic acid and acetic anhydride are the preferred solvents/co-reactants. Acetic acid is the preferred co-reactant of this invention.

Catalysts found to be useful in the method of this invention include borates. Borate compounds are novel for the catalysis of olefins to olefin acetates and diacetates (also called esters and diesters) never having been previously discovered. It is preferred that the catalyst be ammonium borate. This novel catalyst has the formula $NH_4BO_2$ in contrast to the formula of $NH_4HB_4O_7 \cdot 3H_2O$ for ammonium biborate. It is contemplated that the ammonium borate catalyst of this invention could be used in combination with other borate catalysts such as transition metal borates, alkali metal borates and alkali earth metal borates in an effective manner. These catalysts are much less corrosive than many of those used in other methods, especially the halide systems. Also, much smaller catalyst levels may be used. They are also less expensive than many of the catalyst systems proposed.

The reaction conditions under which the method of this invention may be conducted include a temperature range of from 50° to 280° C. A preferred range is from 120° to 220° C. The pressure may be one atmosphere or higher. These conditions are much milder than many of those in the prior art discussed earlier.

An initiator may be optionally used to provide an initial source of free radicals. The use of a readily oxidizable initiator helps to start the oxidation as well as prevent a possible buildup of peroxides which would be dangerous. Aldehydes are suitable initiators with heptaldehyde being the preferred initiator. Usually a few drops are enough to be effective; i.e., quantities on the order of 1.0 ml. Peroxides and azo compounds are also used as initiators.

The invention will be further illustrated by the following examples which are not intended to limit the scope of the invention except as noted. EXAMPLES 1-3

A 1-liter 316 stainless steel glass-lined autoclave equipped with a magnetic stirrer was charged with 300 ml of glacial acetic acid and catalyst. Also present was 1.00 ml of heptaldehyde as an initiator. The autoclave was sealed, 42 g of propylene pressured in, and the mixture heated to the desired temperature. Oxygen was added slowly to a pressure 50-100 psi higher than autogeneous pressure. The pressure was maintained by addition of oxygen from time to time (after each addition of oxygen there was a small exotherm) for the desired reaction time. The reaction mixture was then cooled to room temperature, the reactor vented and the contents analyzed by vapor phase chromatography. The results are shown in Table 1.

Example 2 employed vanadium oxide as a catalyst which is taught by U.S. Pat. No. 4,221,916. Orthoboric acid was employed in Example 3 as taught by U.S. Pat. No. 4,220,800. In Example 1 where the ammonium borate catalyst was used, the weight percent selectivity to esters was higher than for these two comparative Examples 2 and 3.

TABLE I

EXAMPLES ILLUSTRATING THE INVENTION

| Ex. | Catalyst ID | (g) | Temp., °C. | Time, (Hr) | Approx. Conv. % | Esters Selectivity wt. % |
|---|---|---|---|---|---|---|
| 1 | $NH_4BO_2$ | 1.0 | 180 | 5 | 20 | 89.7 |
| 2 | $V_2O_5$ | 1.0 | 160 | 5 | 10 | 63.4 |
| 3 | $H_3BO_3$ | 1.0 | 160 | 6 | 14 | 81.3 |

Many modifications may be made in the method of this invention by those skilled in the art to maximize the yields of the desirable acetates without departing from the spirit and scope of the invention which is defined only by the appended claims. For example, one skilled in the art could determine ammonium borate catalyst concentrations, temperatures, feedstocks and modes of addition to optimize the yield.

We claim:

1. An improved process for the production of alkane hydroxy acetates and diacetates by reacting an olefin or a mixture of olefins with oxygen and a carboxylate ion source selected from the group consisting of acetic acid and acetic anhydride, wherein the improvement comprises conducting the reaction in the presence of ammonium borate.

2. The process of claim 1 in which the reaction is conducted at a temperature in the range of 80° to 280° C.

3. The process of claim 2 in which the reaction is conducted at a temperature between 80° and 180° C.

4. The process of claim 1 in which the olefins have 3 to 16 carbon atoms.

5. The process of claim 1 in which the olefin is propylene.

6. An improved process for the production of alkane hydroxy acetates and diacetates by reacting an olefin or a mixture of olefins where the olefins have 3 to 16 carbon atoms with oxygen and a carboxylate ion source selected from the group consisting of acetic acid and acetic anhydride, at a temperature of between 80° and 180° C., wherein the improvement comprises conducting the reaction in the presence of ammonium borate.

7. The process of claim 6 in which the reaction is conducted at a temperature between 80° and 180° C.

8. The process of claim 6 in which the olefin is propylene.

9. An improved process for the production of alkane hydroxy acetates and diacetates by reacting at least one olefin having 3 to 16 carbon atoms with oxygen and acetic acid at a temperature in the range of 80° to 180° C., wherein the improvement comprises conducting the reaction in the presence of ammonium borate.

10. The process of claim 9 in which the olefin is propylene.

* * * * *